United States Patent
Yamada et al.

(10) Patent No.: US 9,310,660 B2
(45) Date of Patent: Apr. 12, 2016

(54) ORGANIC COMPOUND AND ELECTROCHROMIC ELEMENT INCLUDING THE SAME

(71) Applicant: CANON KABUSHIKI KAISHA, Tokyo (JP)

(72) Inventors: Kenji Yamada, Yokohama (JP); Shinjiro Okada, Kamakura (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/557,283

(22) Filed: Dec. 1, 2014

(65) Prior Publication Data

US 2015/0153624 A1  Jun. 4, 2015

(30) Foreign Application Priority Data

Dec. 3, 2013 (JP) ................. 2013-250401
Oct. 6, 2014 (JP) ................. 2014-206014

(51) Int. Cl.
C07D 409/00 (2006.01)
G02F 1/15 (2006.01)
C07D 495/14 (2006.01)
C07D 409/14 (2006.01)
C07D 495/04 (2006.01)

(52) U.S. Cl.
CPC ............ *G02F 1/1521* (2013.01); *C07D 409/14* (2013.01); *C07D 495/04* (2013.01); *C07D 495/14* (2013.01)

(58) Field of Classification Search
None
See application file for complete search history.

(56) References Cited

U.S. PATENT DOCUMENTS

2013/0100517 A1  4/2013  Yamada

FOREIGN PATENT DOCUMENTS

JP  9-120088 A  5/1997

OTHER PUBLICATIONS

CAPLUS 2008:666523.*
CAPLUS 2012:1417331.*
Guay, J; Kasai, P; Diaz, A, et al., "Chain-Length Dependence of Electrochemical and Electronic Properties . . . " Chemistry of Materials, 1992, vol. 4, No. 5, pp. 1097-1105.
Mei, Jianguo; Heston, Natha C.; Vasilyeva, Svetlana V., et al., "A Facile Approach to Defect-Free Vinylene-Linked Benzothiadiazole-Thiopene . . . ", Macromolecules, vol. 42, No. 5, pp. 1482-1487.

* cited by examiner

*Primary Examiner* — Heidi Reese
(74) *Attorney, Agent, or Firm* — Canon USA Inc. IP Division (57) ABSTRACT

An organic compound represented by Formula [1] showing high transparency in the visible light region is provided.
In Formula [1], $A_1$ to $A_6$ each independently represent a hydrogen atom or a substituent, n is an integer of 1 to 4, and the B's each independently represent a hydrogen atom or a substituent represented by Formula [2], provided that at least one B represents a substituent represented by Formula [2]. In Formula [2], $R_2$ represents a substituent.

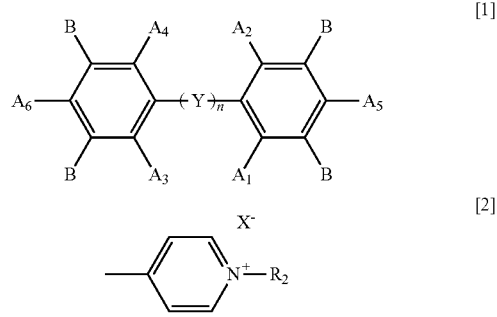

14 Claims, 2 Drawing Sheets

ORGANIC COMPOUND AND ELECTROCHROMIC ELEMENT INCLUDING THE SAME

BACKGROUND OF THE INVENTION

1. Field of the Invention

The present invention relates to a novel organic electrochromic compound and an electrochromic element including the same.

2. Description of the Related Art

Various materials have been reported as electrochromic (hereinafter, may be abbreviated to "EC") materials that vary their optical absorption properties (colored state and light transmittance) by electrochemical redox reactions. Though metal oxides such as $WO_3$ are known as inorganic EC materials, the method of forming a film from such a metal oxide is limited to, for example, deposition, which disadvantageously prevents formation of a large-size film.

As organic EC materials, for example, conductive polymers such as polythiophene and polyaniline and low-molecular-weight organic compounds such as viologen and oligothiophene are known.

Examples of the low-molecular-weight organic EC compounds include viologen derivatives (cathodic compounds) coloring by reduction and oligothiophene derivatives (anodic compounds) coloring by oxidations.

These low-molecular-weight EC compounds have a shorter π conjugation length compared to the conductive polymers and have absorption in the ultraviolet region. The compounds therefore transmit visible light in a neutralized state and absorb visible light in an oxidized state (in a case of anodic compounds) or in a reduced state (in a case of cathodic compounds). That is, since the conjugation length in an oxidized state or a reduced state is longer than that in a neutralized state, the wavelength region absorbing light shifts to the visible light region.

In other words, the low-molecular-weight EC compounds discolor in a neutralized state and color in an oxidized state or a reduced state.

Japanese Patent Laid-Open No. 9-120088 describes a viologen derivative coloring in a reduced state. An oligothiophene derivative that colors in an oxidized state is described in GUAY, J; KASAI, P; DIAZ, A, et al., Chemistry of Materials, 1992, vol. 4, No. 5, pp. 1097-1105. U.S. Patent Application Publication No. 2013/0100517 describes an organic compound having dithienothiophene and describes an electrochromic element including the organic compound having dithienothiophene.

An EC element including a low-molecular-weight organic EC compound shows high transparency in its discoloring. As an EC element including a low-molecular-weight organic EC compound, a sandwich-type element in which an EC compound dissolved in a solvent such as propylene carbonate is disposed between a pair of electrodes is known.

The optical density (low transmittance) in the coloring of a low-molecular-weight EC compound can be increased by dissolving the low-molecular-weight EC compound in a solvent at a high concentration.

The oligothiophene derivative described in Chemistry of Materials, 1992, vol. 4, No. 5, pp. 1097-1105 has a low solubility in a solvent and is unstable when a redox reaction is repeated.

The viologen derivative (cathodic compound) described in Japanese Patent Laid-Open No. 9-120088 has a high solubility due to its molecular structure, but is unstable when a redox reaction is repeated. The organic compound described in U.S. Patent Application Publication No. 2013/0100517 has insufficient solubility in a solvent such as propylene carbonate.

SUMMARY OF THE INVENTION

Aspects of present invention provide an organic compound having a high solubility in an organic solvent and having anodic electrochromic properties showing high stability against repetition of a redox reaction.

Accordingly, aspects of the present invention provide an organic compound represented by Formula [1]:

[1]

wherein, $A_1$ to $A_6$ each independently represent a substituent selected from a hydrogen atom, alkyl groups having 1 to 20 carbon atoms, alkoxy groups having 1 to 20 carbon atoms, and optionally substituted aryl groups, wherein a substituent of the optionally substituted aryl group is selected from halogen atoms, alkyl groups having 1 to 4 carbon atoms, alkoxy groups having 1 to 4 carbon atoms, aryl groups, aralkyl groups, substituted amino groups, and substituted silyl groups;

n is an integer of 1 to 4;

B's each independently represent a hydrogen atom or a substituent represented by Formula [2], provided that at least one of four B's represents a substituent represented by Formula [2]:

[2]

wherein $X^-$ represents an anion, and $R_2$ represents an optionally substituted alkyl group having 1 to 20 carbon atoms or an optionally substituted aryl group;

Y represents a structure represented by any one of Formulae [3] to [6], provided that when n represents a number of 2 or more, Y's are each independently selected from Formulae [3] to [6]:

[3]

[4]

wherein, $R_3$ represents an alkylene group having 1 to 20 carbon atoms, and $R_4$ to $R_9$ are each independently selected from a hydrogen atom, halogen atoms, alkyl groups having 1 to 20 carbon atoms, alkoxy groups having 1 to 20 carbon atoms, optionally substituted aryl groups, alkyl ester groups having 1 to 20 carbon atoms, optionally substituted amino groups, and a cyano group.

Further features of the present invention will become apparent from the following description of exemplary embodiments with reference to the attached drawings.

DESCRIPTION OF THE EMBODIMENTS

The present invention relates to an organic compound having electrochromic properties. The organic compound having electrochromic properties is also called an electrochromic compound. The organic compound according to the present invention is represented by Formula [1]:

The organic compound represented by Formula [1] includes a thiophene derivative represented by Y and phenyl groups being linked to the thiophene derivative and having a pyridinium salt.

$A_1$ to $A_6$ in Formula [1] each independently represent a substituent selected from a hydrogen atom, alkyl groups having 1 to 20 carbon atoms, alkoxy groups having 1 to 20 carbon atoms, and optionally substituted aryl groups.

In the embodiment, the alkyl groups having 1 to 20 carbon atoms may be linear, branched, or cyclic.

In the embodiment, alkyl groups, alkoxy groups, and other groups may be linear, branched, or cyclic, unless specified otherwise.

The alkyl group represented by $A_1$ to $A_6$ preferably has 1 to 6 carbon atoms and more preferably 1 or 2 carbon atoms.

Examples of the alkyl group include methyl group, ethyl group, n-propyl group, isopropyl group, n-butyl group, tert-butyl group, pentyl group, hexyl group, octyl group, dodecyl group, cyclohexyl group, bicyclooctyl group, and adamantyl group. Furthermore, a hydrogen atom of the alkyl group may be replaced by a fluorine atom, for example, by a trifluoromethyl group.

In particular, the alkyl group can be a methyl, ethyl, n-butyl, or hexyl group and more particularly a methyl or ethyl group.

The alkoxy group having 1 to 20 carbon atoms represented by $A_1$ to $A_6$ may be linear, branched, or cyclic and preferably have 1 to 8 carbon atoms.

Examples of the alkoxy group include methoxy group, ethoxy group, isopropoxy group, n-butoxy group, tert-butoxy group, ethylhexyloxy group, and octyloxy group. In particular, the alkoxy group can be a methoxy, ethoxy, or isopropoxy group.

Examples of the aryl group represented by $A_1$ to $A_6$ include phenyl group, biphenyl group, fluorenyl group, naphthyl group, fluoranthenyl group, anthryl group, phenanthryl group, pyrenyl group, and perylenyl group. In particular, the aryl group can be a phenyl group.

Examples of the heteroatom-containing aryl group (heterocyclic group) include pyridyl group and indolyl group. In particular, the aryl group can be a pyridyl group.

The aryl group may have, as a substituent, a halogen atom, alkyl group having 1 to 4 carbon atoms, alkoxy group having 1 to 4 carbon atoms, aryl group, aralkyl group, substituted amino group, or substituted silyl group.

Examples of the aryl group, aralkyl group, substituted amino group, or substituted silyl group as the substituent of the aryl group include phenyl group, biphenyl group, naphthyl group, benzyl group, dimethylamino group, diphenylamino group, and triisopropylsilyl group.

In Formula [1] according to the embodiment, B represents a hydrogen atom or a substituent having a pyridinium salt structure represented by Formula [2], provided that at least one of four B's represents a substituent having a pyridinium salt structure represented by Formula [2] and the remaining B's are hydrogen atoms.

In Formula [2], $X^-$ represents an anion. When the compound represented by Formula [1] includes a plurality of pyridinium salts, the anions represented by $X^-$ may be the same or different.

Examples of the anion represented by $X^-$ include $PF_6^-$, $ClO_4^-$, $BF_4^-$, $AsF_6^-$, $SbF_6^-$, $CF_3SO_3^-$, $(CF_3SO_2)_2N^-$, and halogen anions such as $Br^-$, $Cl^-$, and $I^-$. In particular, the anion can be $PF_6^-$, $ClO_4^-$, $BF_4^-$, or $(CF_3SO_2)_2N^-$.

$R_2$ represents an optionally substituted alkyl group having 1 to 20 carbon atoms or an optionally substituted aryl group. The alkyl group having 1 to 20 carbon atoms represented by $R_2$ may be linear, branched, or cyclic.

Examples of the alkyl group include methyl group, ethyl group, n-propyl group, isopropyl group, n-butyl group, tert-butyl group, pentyl group, hexyl group, heptyl group, octyl group, dodecyl group, cyclohexyl group, bicyclooctyl group, and adamantyl group. Furthermore, a hydrogen atom of the alkyl group may be replaced by an aromatic ring, for example, by a benzyl group.

Examples of the aryl group represented by $R_2$ include phenyl group, biphenyl group, fluorenyl group, naphthyl group, fluoranthenyl group, and anthryl group. In particular, the aryl group can be a phenyl group.

In Formula [1], Y is a thiophene derivative represented by any one of Formulae [3] to [6]; and n represents an integer of 1 to 4. When n represents an integer of 2 or more, the plurality of Y's may be the same or different. The thiophene derivative is a compound showing an EC property of coloring when oxidized.

[3]

[4]

[5]

[6]

In Formula [3], the alkylene group represented by $R_3$ is an alkylene group having 1 to 20 carbon atoms and can be an alkylene group having 1 to 4 carbon atoms.

Examples of the alkylene group include methylene group, ethylene group, n-propylene group, n-butylene group, isopropylene group, and isobutylene group.

In Formulae [4] to [6], $R_4$ to $R_9$ are each independently selected from a hydrogen atom, halogen atoms, alkyl groups having 1 to 20 carbon atoms, alkoxy groups having 1 to 20 carbon atoms, optionally substituted aryl groups, alkyl ester groups having 1 to 20 carbon atoms, optionally substituted amino groups, and a cyano group.

The alkyl group having 1 to 20 carbon atoms represented by $R_4$ to $R_9$ may be linear, branched, or cyclic. The alkyl group preferably has 1 to 6 carbon atoms and more preferably 1 or 2 carbon atoms.

Examples of the alkyl group include methyl group, ethyl group, n-propyl group, isopropyl group, n-butyl group, tert-butyl group, pentyl group, hexyl group, octyl group, dodecyl group, cyclohexyl group, bicyclooctyl group, and adamantyl group. Furthermore, a hydrogen atom of the alkyl group may be replaced by a fluorine atom, for example, by a trifluoromethyl group.

In particular, the alkyl group can be a methyl, ethyl, n-butyl, or hexyl group and more particularly a methyl or ethyl group.

The alkoxy group having 1 to 20 carbon atoms represented by $R_4$ to $R_9$ may be linear, branched, or cyclic and preferably has 1 to 8 carbon atoms.

Examples of the alkoxy group include methoxy group, ethoxy group, isopropoxy group, n-butoxy group, tert-butoxy group, ethylhexyloxy group, and octyloxy group.

Examples of the aryl group represented by $R_4$ to $R_9$ include phenyl group, biphenyl group, fluorenyl group, naphthyl group, fluoranthenyl group, and anthryl group. In particular, the aryl group can be a phenyl group. The aryl group represented by $R_4$ to $R_9$ may have, as a substituent, an alkyl group having 1 to 8 carbon atoms or an alkoxy group having 1 to 8 carbon atoms.

Examples of the alkyl ester group having 1 to 20 carbon atoms represented by $R_4$ to $R_9$ include methyl ester groups, ethyl ester groups, n-propyl ester groups, isopropyl ester groups, n-butyl ester groups, tert-butyl ester groups, tert-amyl ester groups, hexyl ester groups, heptyl ester groups, octyl ester groups, ethylhexyl ester groups, cyclopentyl ester groups, and cyclohexyl ester groups.

The organic compound according to the present invention has a structure in which a phenyl group is introduced at the 2-position or 5-position of thiophene, and is therefore highly stable in a radical cation state.

Furthermore, the compound represented by Formula [1] in which $A_1$ to $A_4$ are substituents other than hydrogen atoms is highly stable in a radical cation state.

That is, $A_1$ to $A_4$ in Formula [1] according to the present invention can each be an alkyl group, an alkoxy group, or an aryl group.

The substituents mentioned above as $A_1$ to $A_4$ protect the thiophene derivative of the EC moiety represented by Y in Formula [1], by steric hindrance.

In the organic compound according to the present invention, when $A_1$ to $A_4$ are substituents other than hydrogen atoms, these substituents form a molecular structure surrounding the thiophene moiety represented by Y. Consequently, the radical cation moiety generated by an electrochemical reaction can be prevented from approaching other electrochromic molecules and impurities.

Accordingly, at least one of $A_1$ to $A_4$ should be a substituent. In particular, all of $A_1$ to $A_4$ can be substituents other than hydrogen atoms.

The organic compound according to the present invention has substituents represented by $A_1$ to $A_4$ that prevent other molecules from approaching the thiophene derivative, which reduces the risk of the reaction of the thiophene derivative with another molecule. As a result, the stability of the compound is high.

The substituents represented by $A_1$ to $A_4$ can be alkyl groups such as a methyl group or alkoxy groups such as a methoxy group and an isopropoxy group. These substituents are electron-donating substituents and have an effect of enhancing the stability of electron-poor radical cations.

B in Formula [1] will now be described. B in Formula [1] is represented by Formula [2]. Formula [2] shows a substituent having a pyridinium salt structure.

The organic compound according to the present invention has the substituent represented by Formula [2] at a meta-position of a phenyl group and therefore has high solubility in a polar solvent.

The pyridinium salt structure of the organic compound according to the present invention has a high affinity to a polar solvent. Consequently, the compound can be dissolved in a polar solvent at a high concentration.

It is believed that even if the pyridinium salt structure moiety of the organic compound according to the present invention is replaced by a pyridine ring, the resulting compound has an effect of enhancing the solubility to a certain degree, but a compound having the pyridinium salt structure has higher solubility.

Exemplified compound A-17 described in US Patent Application No. 2013/0100517 has a solubility of 1 mM, and exemplified compound XX-8 has a solubility of 7 mM. The solubilities of other exemplified compounds in propylene carbonate are within a range of about 1 to 10 mM. In contrast, the solubility of the organic compound according to the present invention in propylene carbonate is within a range of 20 to 500 mM. Thus, it is demonstrated that the solubility is notably increased.

The organic compound according to the present invention has a short π conjugation system and does not have absorption bands in the visible light region in a neutral state and therefore has high transparency.

However, if the pyridinium salt structure is located at the ortho- or para-position of a phenyl group represented by Formula [1], the π electron system of the thiophene ring serving as the EC moiety or the terminal phenyl group electronically resonates with the π electron system of the pyridine ring. Consequently, the effective conjugation length is elongated as the entire molecule, and the absorption shifts to the longer wavelength.

As a result, the compound has an absorption band in the visible light region even in a neutral state, and the high transparency may be deteriorated.

On the other hand, in the organic compound according to the present invention, the pyridinium salt structure is located at the meta-position of the phenyl group represented by Formula [1], which reduces the risk of resonance of the π electron system of the thiophene ring or the phenyl group with the π electron system of the pyridinium salt structure.

As a result, the compound can have high transparency in a neutral state.

The organic compound according to the present invention has EC properties and can therefore be used in an electrochromic element (EC element). The organic compound according to the present invention has high solubility in a polar solvent and can therefore be used, in particular, in a solution-type EC element having an electrochromic layer constituted of a solution.

Specific structural formulae of the compound according to the present invention are exemplified below, but the compounds according to the present invention are not limited to the following compounds.

A-1

A-2

A-3

A-4

A-5

-continued

A-6

A-7

A-8

B-1

B-2

B-3

B-4

B-5

B-6

B-7

B-8

B-9

B-10

B-11

B-12

The compounds belonging to Group A in the exemplified compounds have a chemical structure in which the oxidation coloring moiety Y in Formula [1] is dithienothiophene and the pyridinium salt structure represented by B in Formula [1] is located at the meta-position of the phenyl group.

In Group A, $A_1$ to $A_4$ may be hydrogen atoms.

The compounds belonging to Group B have a chemical structure in which the moiety represented by Y in Formula [1] is a thiophene derivative and n is an integer of 1 to 4.

In all compounds mentioned above, the pyridinium salt structure represented by B is located at the meta-position of the phenyl group and therefore contributes to enhancement of solubility without affecting the absorption properties and the EC properties of the molecule.

Accordingly, the organic EC compounds according to the present invention have high solubility in organic solvents and do not have absorption bands in the visible light region in their discoloring to show high transparency.

(Method of Synthesizing Organic Compound According to the Present Invention)

The organic compound according to the present invention can be synthesized by, for example, the following methods: 1) a method by performing a coupling reaction between a phenyl group having a halogen substituent at a meta-position and a thiophene compound as an EC moiety, reacting a halogen atom with a pyridyl group, and then converting the pyridyl group into a pyridinium salt; or 2) a method by synthesizing a phenyl group having a pyridyl group substituent and a thiophene derivative serving as an EC moiety, being linked to the phenyl group and the thiophene derivative by a coupling reaction, and then converting the pyridyl group into a pyridinium salt.

In the EC organic compounds according to the embodiment, the coupling reaction of a combination of a halogen and boronic acid (or boronic ester) can be carried out using a known Pd catalyst.

As an example of the synthesis, a synthesis scheme of a coupling reaction between a compound having 2,2'-bithiophene as the EC moiety represented by Y and a compound as a phenyl group having a pyridyl group substituent at a meta-position represented by Formula [1] is shown below.

In the synthesis scheme, X represents a halogen atom. The X⁻ reacts with the pyridyl group of the organic compound prepared by the coupling reaction to synthesize an organic compound according to the present invention. The EC organic compounds according to the embodiment can be synthesized using other thiophene derivatives instead of the 2,2'-bithiophene structure in the following synthesis scheme.

The EC organic compound according to the present invention can be used as an EC layer of an electrochromic element.

Figure 1:
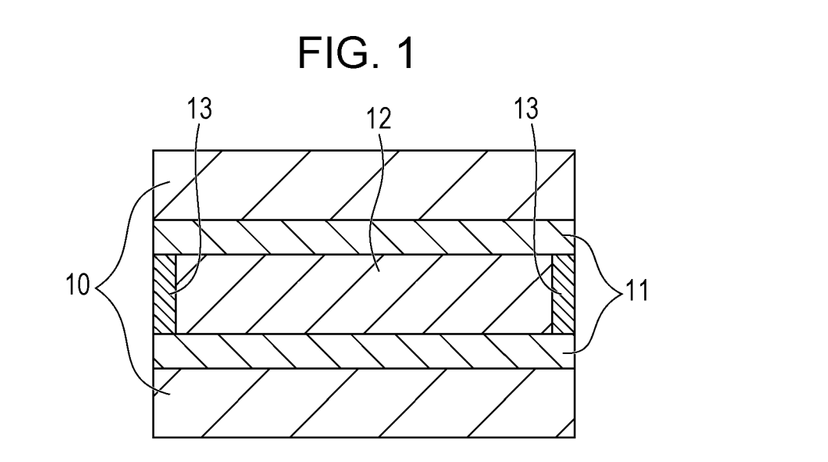
FIG. 1 is a schematic cross-sectional view of an example of an electrochromic element according to an embodiment.

An EC element according to an embodiment will now be described with reference to a drawing.

The EC element shown in FIG. 1 includes a pair of transparent electrodes 11 and an EC layer 12 disposed between the pair of electrodes and containing an electrolyte and an EC organic compound according to the present invention. A constant interelectrode distance is maintained with a spacer 13 between the pair of electrodes. In this EC element, the pair of electrodes is disposed between a pair of transparent substrates 10.

The EC layer 12 includes an organic compound according to the present invention and an electrolyte. The EC layer may have a layer of an EC compound and a layer of an electrolyte. Alternatively, the EC layer may be a solution containing an EC compound and an electrolyte. In the EC element according to this embodiment, the EC layer can be a solution.

Each member constituting the EC element according to this embodiment will now be described.

The electrolyte may be any ion dissociating salt that shows satisfactory solubility in a solvent or high compatibility in a solid electrolyte. In particular, an electron-donating electrolyte can be used. These electrolytes can be also called supporting electrolytes.

Examples of the electrolyte include inorganic ionic salts such as various alkali metal salts and alkaline earth metal salts, quaternary ammonium salts, and cyclic quaternary ammonium salts.

More specifically, examples of the electrolyte include alkali metal salts of Li, Na, and K such as $LiClO_4$, $LiSCN$, $LiBF_4$, $LiAsF_6$, $LiCF_3SO_3$, $LiPF_6$, LiI, NaI, NaSCN, $NaClO_4$, $NaBF_4$, $NaAsF_6$, KSCN, and KCl; and quaternary ammonium salts and cyclic quaternary ammonium salts such as $(CH_3)_4NBF_4$, $(C_2H_5)_4NBF_4$, $(n-C_4H_9)_4NBF_4$, $(n-C_4H_9)_4NPF_6$, $(C_2H_5)_4NBr$, $(C_2H_5)_4NClO_4$, and $(n-C_4H_9)_4NClO_4$.

The solvent for dissolving the EC organic compound and the electrolyte may be any solvent that can dissolve an EC organic compound and an electrolyte and, in particular, can be a solvent having polarity.

Examples of the solvent include water and organic polar solvents such as methanol, ethanol, propylene carbonate, ethylene carbonate, dimethyl sulfoxide, dimethoxyethane, γ-butyrolactone, γ-valerolactone, sulfolane, dimethyl formamide, dimethoxyethane, tetrahydrofuran, acetonitrile, propionitrile, benzonitrile, dimethylacetamide, methylpyrrolidinone, and dioxolane.

Furthermore, a solvent having a high viscosity or being in a gel form prepared by adding a polymer or a gelling agent to the EC solvent can also be used.

The polymer is not particularly limited, and examples thereof include polyacrylonitrile, carboxymethyl cellulose, polyvinyl chloride, polyethylene oxide, polypropylene oxide, polyurethane, polyacrylate, polymethacrylate, polyamide, polyacrylamide, polyester, and Nafion (registered trademark).

The transparent substrates and the transparent electrodes will now be described. As the transparent substrates 10, for example, colorless or colored glass or tempered glass or a colorless or colored transparent resin is used. In this embodiment, the term "transparent" refers to a visible light transmittance of 90% or more.

Examples of the transparent resin include polyethylene terephthalates, polyethylene naphthalates, polynorbornenes, polyamides, polysulfones, polyether sulfones, polyether ether ketones, polyphenylene sulfides, polycarbonates, polyimides, and polymethyl methacrylate.

Examples of the material of the electrodes 11 include metals and metal oxides such as indium tin oxide (ITO) alloys, fluorine-doped tin oxide (FTO), tin oxide (NESA), indium zinc oxide (IZO), silver oxide, vanadium oxide, molybdenum oxide, gold, silver, platinum, copper, indium, and chromium; silicon materials such as polycrystalline silicon and amorphous silicon; and carbon materials such as carbon black, graphite, and glassy carbon.

In addition, conductive polymers, such as polyaniline, polypyrrole, polythiophene, polyacetylene, polyparaphenylene, and polyethylene dioxythiophene (PEDOT)-polystyrene sulfonate complexes, having improved conductivity by, for example, doping can also be used.

The spacer 13 is disposed between the pair of electrodes 11 and provides a space for accommodating a solution 12 containing the EC organic compound of the present invention. Specifically, the spacer 13 can be formed of, for example, a polyimide, polytetrafluoroethylene, fluororubber, or an epoxy resin. The spacer can maintain the interelectrode distance of the EC element.

The EC element according to the embodiment may have a liquid inlet formed by the pair of electrodes and the spacer. A composition containing the EC organic compound is put into the space through the liquid inlet, and the inlet is covered with a sealing member and is further sealed with, for example, an adhesive to form an element.

The sealing member also functions to isolate the adhesive from the EC organic compound not to contact with each other. The sealing member may have any shape and can have a tapered shape such as a wedge-shape.

The EC element according to the embodiment may be formed by any method and can be produced by injecting a solution 12 containing an EC organic compound prepared in advance by, for example, vacuum injection, air injection, or a meniscus method into the gap formed between a pair of electrode substrates.

The EC element according to the embodiment may contain the organic compound according to the present invention and a second organic compound that is a different type than the organic compound. The second organic compound may be a single organic compound or a mixture of different organic compounds and may be a compound coloring in an oxidized state, a compound coloring in a reduced state, or both compounds. In particular, a compound coloring in a reduced state can be used.

The compound coloring in a reduced state has a visible light transmittance in a reduced state lower than that in an oxidized state.

The second EC compound in the coloring has an absorption wavelength region preferably in a range of 400 nm or more and 800 nm or less and more preferably in the range of 420 nm or more and 700 nm or less.

In the EC element containing a second EC compound according to the embodiment, the difference between the maximum visible-light absorptivity in the coloring of the EC element and the minimum visible-light absorptivity in the coloring can be 34% or less. The difference in the light absorptivity can be further 10% or less.

Color shift in the coloring can be reduced by using an EC element showing a smaller difference in light absorptivity at each wavelength in the visible light region.

When an EC element uniformly absorbing light in the visible light region is colored, the EC element shows less color shift in the coloring and discoloring.

The compound used in the EC element can have an absorption wavelength peak of 400 nm or less in either an oxidized state or a reduced state. An element having high transparency can be provided by reducing the light transmittance of the EC element.

Other examples of the EC compound according to the embodiment include the following compounds.

Other examples of the EC compound coloring in an oxidized state include phenazine compounds such as 5,10-dihydro-5,10-dimethylphenazine and 5,10-dihydro-5,10-diethylphenazine; metallocene-based compounds such as ferrocene, tetra-t-butylferrocene, and titanocene; phenylenediamine compounds such as N,N',N,N'-tetramethyl-p-phenylenediamine; and pyrazoline compounds such as 1-phenyl-2-pyrazoline.

Other examples of the compound coloring in a reduced state include viologen compounds such as N,N'-diheptylbipyridinium diperchlorate, N,N'-diheptylbipyridinium ditetrafluoroborate, N,N'-diheptylbipyridinium dihexafluorophosphate, N,N'-diethylbipyridinium diperchlorate, N,N'-diethylbipyridinium ditetrafluoroborate, N,N'-diethylbipyridinium dihexafluorophosphate, N,N'-dibenzylbipyridinium diperchlorate, N,N'- dibenzylbipyridinium ditetrafluoroborate, N,N'-dibenzylbipyridinium dihexafluorophosphate, N,N'-diphenylbipyridinium diperchlorate, N,N'-diphenylbipyridinium ditetrafluoroborate, and N,N'-diphenylbipyridinium dihexafluorophosphate; anthraquinone compounds such as 2-ethylanthraquinone, 2-t-butylanthraquinone, and octamethylanthraquinone; ferrocenium salt compounds such as ferrocenium tetrafluoroborate and ferrocenium hexafluorophosphate; and styryl compounds.

The electrochromic element according to the present invention has an excellent durability when the element includes a compound coloring in an oxidized state according to the present invention and a compound of the pyridinium salt coloring in a reduced state as the electrochromic compounds, compared when the element includes an organic compound coloring in an oxidized state and not having a pyridinium salt and a compound of a bipyridinium salt coloring in a reduced state as the electrochromic compounds. This may be caused by that the electrostatic repulsion between the cationic pyridinium salt in the organic compound molecule according to the present invention and the cationic bipyridinium salt coloring in a reduced state prevents intermolecular collision.

The EC element according to the embodiment shows high transparency in the discoloring, and the organic compound according to the present invention has high solubility in an organic solvent. Consequently, the EC element can provide a high optical density in the coloring to decrease the transmittance and therefore can be used for considerably reducing the quantity of incident light on an image pickup device such as a camera.

The EC element according to the embodiment can be used in optical filters, lens units, image pick-up apparatuses, and window applications.

The optical filter includes the EC element according to the embodiment and an active device connected to the EC element. The active device may be directly connected or indirectly connected to the EC element. An example of the active device is a switching device for controlling the transmittance of the EC element. Examples of the switching device include TFTs and metal-insulator-metal (MIM) devices. The TFT is also called thin film transistor. The constituent material of the TFT is a semiconductor or an oxide semiconductor. Specifically, the constituent material of the semiconductor may be amorphous silicon, low-temperature poly-silicon, or InGaZnO.

The lens unit according to the embodiment includes a plurality of lenses and an optical filter including an EC element. The optical filter may be disposed between the lenses or outside the lenses. The optical filter can be disposed on the optical axis of the lenses.

The image pick-up apparatus according to the embodiment includes an optical filter and a light receiving device receiving light passed through the optical filter.

Examples of the image pick-up apparatus include cameras, video cameras, and mobile phones equipped with cameras. The image pick-up apparatus may be in a form capable of being separated into a body including a light receiving device and a lens unit including a lens.

In the form allowing the lens unit to be separated from the image pick-up apparatus body, an additional optical filter may be used in image pickup. The optical filter may be disposed outside the lens unit, between the lens unit and the light receiving device, or between lenses when the lens unit includes a plurality of lenses.

The window application according to the embodiment includes a pair of transparent substrates, an EC element, and an active device for controlling the transmittance of the EC element. The active device is connected to the EC element. The active device may be directly connected or indirectly connected to the EC element. The window application can be used in the window of an airplane, automobile, house, etc.

The window application including an EC element can also be called a window application with an electronic curtain.

Figure 3:
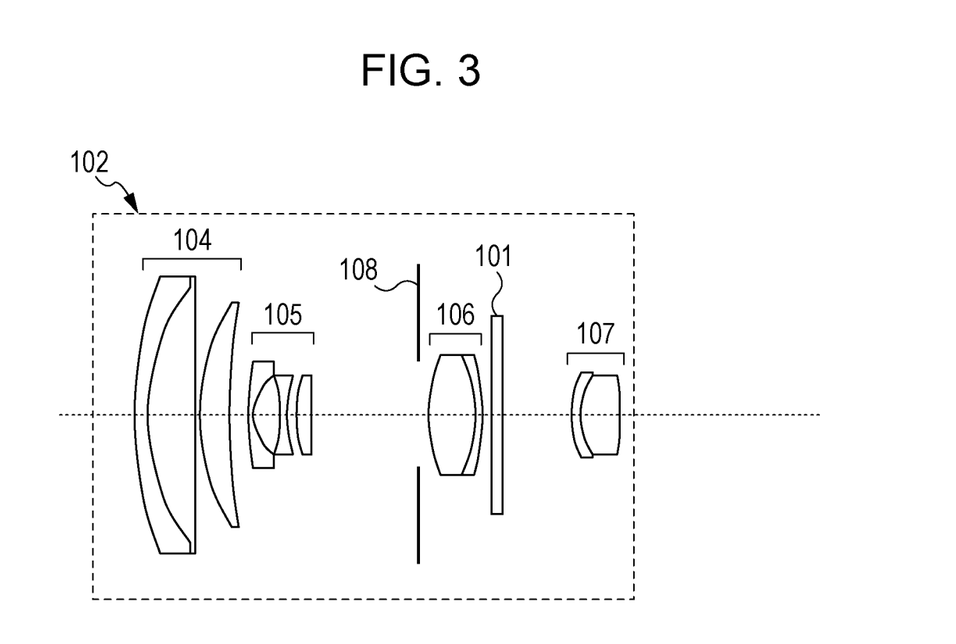
FIG. 3 is a schematic cross-sectional view of a lens unit according to an embodiment.

FIG. 3 is a schematic view illustrating an optical filter according to the embodiment and a lens unit including the filter.

The optical filter 101 includes an organic EC element and an active device connected to the organic EC element and is disposed inside the lens unit 102.

The lens unit 102 includes a plurality of lenses or a plurality of lens groups. For example, in FIG. 3, the lens unit includes four lenses: a first lens 104, a second lens 105, a third lens 106, and fourth lens 107. Each of the four lenses may be composed of a plurality of lenses. The number of lenses is not limited to four.

For example, the lens unit varies the magnification by changing the distance between the second lens and the third lens and focuses by moving the fourth lens.

The lens unit 102 has a structure, for example, including an aperture diaphragm 108 between the second lens and the third lens and an optical filter 101 between the third lens and the fourth lens. Alternatively, the optical filter may be disposed at another position, for example, between the first lens and the second lens.

Figure 4:
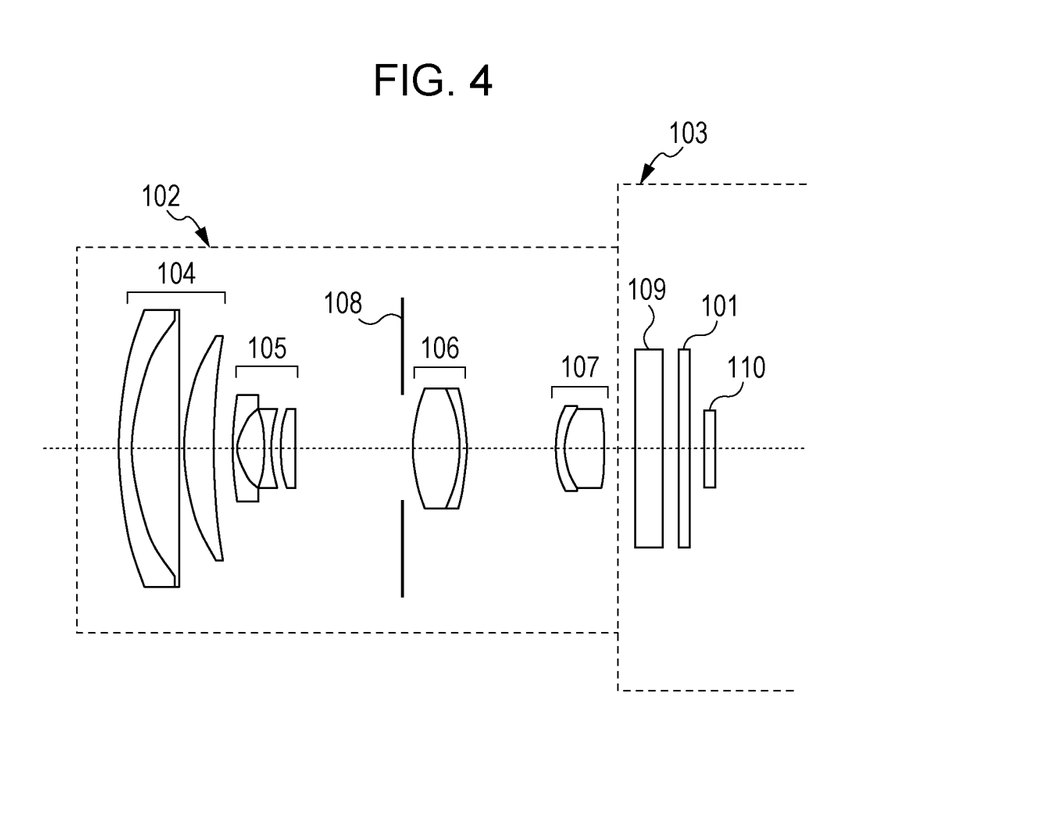
FIG. 4 is a schematic cross-sectional view of an image pick-up apparatus according to an embodiment.

FIG. 4 is a schematic view illustrating an image pick-up apparatus including the optical filter according to the embodiment. The components of the lens unit 102 are the same as those shown in FIG. 3.

The lens unit 102 is detachably connected to the image pick-up apparatus 103 via a mount member (not shown).

The glass block 109 is, for example, a low pass filter, face plate, or color filter.

The light receiving device 110 is a sensor unit for receiving light passed through the lens unit and can be an image pickup device such as a CCD or CMOS. Alternatively, the light receiving device 110 may be a photosensor such as a photodiode. A device that obtains information on intensity or wavelength of light and output it can be appropriately used.

In FIG. 4, the optical filter 101 is disposed just before the light receiving device 110. The embodiment is not limited to this arrangement, and the optical filter 101 may be disposed, for example, between the forth lens and the glass block 109.

The EC element has optical characteristics such that high transparency is exhibited in the discoloring to transmit a sufficient intensity of incident light and that in the coloring, incident light is surely shielded and is modulated. In addition, the EC element has excellent redox repetition characteristics and can therefore have a long lifetime.

EXAMPLES

The present invention will now be further specifically described by examples, but is not limited to the following examples. Desired EC organic compounds can be synthesized by appropriately modifying the moiety showing EC properties in the example and the substituents of the phenyl groups in the structure.

Example 1

Synthesis of Exemplified Compound A-1

(1) Synthesis of XX-3: In a 1-L reaction container, 6.03 g (21.8 mmol) of 2-bromo-dithienothiophene and 7.16 g (43.7 mmol) of 2,4,6-trimethylphenylboronic acid were mixed in 437 mL of toluene, and dissolved oxygen was removed by nitrogen.

Subsequently, 98 mg (0.437 mmol) of Pd(OAc)$_2$, 448 mg (1.09 mmol) of 2-dicyclohexylphosphino-2',6'-dimethoxybiphenyl (S-Phos), and 23.2 g (109.2 mmol) of tripotassium phosphate were added to the mixture under a nitrogen atmosphere, followed by heating to reflux at 140° C. for 24 hours.

The reaction solution was cooled to room temperature, concentrated under reduced pressure, and subjected to silica gel chromatography (mobile phase: heptane/chloroform=9/1) for isolation and purification to obtain XX-2 (4.66 g, yield: 67.6%) as a yellow oil.

Subsequently, in a 500-mL reaction container, 2.4 g (7.63 mmol) of the resulting XX-2 was dissolved in anhydrous tetrahydrofuran, and the solution was cooled to −78° C. A solution of 1.65 M n-butyllithium in hexane (5.09 mL, 8.39 mmol) was dropwise added to the solution under an argon atmosphere, followed by stirring for 30 minutes. The 2.34 mL (11.45 mmol) of isopropoxy pinacolborane was added to the mixture, followed by reaction at room temperature for 1.5 hours.

Water was added to the reaction solution to stop the reaction, followed by concentration under reduced pressure. The residue was dispersed and washed in methanol to obtain XX-3 (3.05 g, yield: 90.7%).

(2) Synthesis of XX-5: In a 100-mL reaction container, 661 mg (1.5 mmol) of XX-3 and 566 mg (2.0 mmol) of 1-bromo-3-iodobenzene were mixed in a solvent mixture of toluene (6 mL) and ethanol (3 mL), and dissolved oxygen was removed by nitrogen.

Subsequently, 57.8 mg (0.05 mmol) of Pd(PPh$_3$)$_4$ and 6 mL of an aqueous solution of 1 M sodium carbonate were added to the mixture under a nitrogen atmosphere, followed by heating at 65° C. for 7 hours for reaction.

The reaction solution was cooled to room temperature, concentrated under reduced pressure, and subjected to silica gel chromatography (mobile phase: hexane/chloroform=9/1) for isolation and purification to obtain XX-4 (0.74 g).

Subsequently, in a 100-mL reaction container, 260 mg (0.55 mmol) of the resulting XX-4 and 147 mg (0.715 mmol) of 4-pyridylboronic acid pinacol ester were mixed in a solvent mixture of toluene (6 mL) and ethanol (3 mL), and dissolved oxygen was removed by nitrogen. Subsequently, 24 mg (0.02 mmol) of Pd(PPh$_3$)$_4$ and 6 mL of an aqueous solution of 1 M sodium carbonate were added to the mixture under a nitrogen atmosphere, followed by heating at 80° C. for 6 hours for reaction.

The reaction solution was cooled to room temperature, concentrated under reduced pressure, and subjected to silica gel chromatography (mobile phase: ethyl acetate) for isolation and purification to obtain XX-5 (257 mg).

(3) Synthesis of A-1: In a 25-mL reaction container, 217 mg (0.46 mmol) of XX-5 and 156 mg (0.63 mmol) of benzyl bromide were dissolved in toluene (6 mL), followed by reaction at 110° C. for 4 hours.

The reaction solution was cooled to room temperature, and the resulting light yellow precipitate was collected by filtration. Ethyl acetate (40 mL) and water (50 mL) were added to the precipitate, followed by stirring. KPF$_6$ (1.5 g) was added to the aqueous layer, followed by an anion exchange reaction. Ethyl acetate was further added to the aqueous layer, and the organic layer was collected and concentrated to obtain target compound A-1 (142 mg).

The structure of the resulting compound was verified by nuclear magnetic resonance spectrometry (NMR). As a result, the ratio of integrated values of peaks well agreed with the structure of compound A-1, which demonstrates that the resulting compound is exemplified compound A-1. The measurement results of the NMR spectrum are shown below:

$^1$H-NMR (THF-d$_8$) δ (ppm): 9.14 (d, 2H), 8.57 (d, 2H), 8.45 (s, 1H), 8.39 (s, 1H), 8.02-7.97 (m, 2H), 7.73 (t, 1H), 7.66 (d, 2H), 7.55-7.47 (m, 3H), 7.21 (s, 1H), 7.03 (s, 1H), 5.94 (s, 2H), 2.38 (s, 3H), 2.26 (s, 6H).

Figure 2:
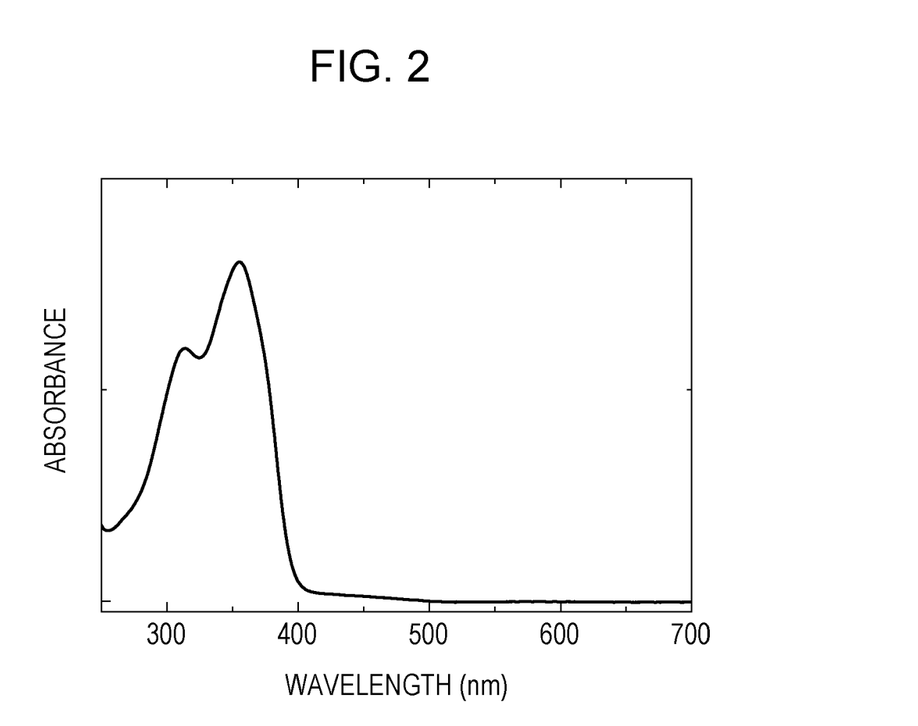
FIG. 2 is a graph showing an ultraviolet and visible absorption spectrum of exemplified compound A-1 in a neutralized state.

The resulting exemplified compound A-1 was dissolved in chloroform. The absorption spectrum of the solution was measured with an ultraviolet and visible spectrometer (V-560, manufactured by JASCO Corp.) and is shown in FIG. 2.

The maximum absorption peak λmax was observed at 355.5 nm in the ultraviolet region. Exemplified compound A-1 does not have absorption over the entire visible light region and is therefore a transparent material.

Example 2

Synthesis of Exemplified Compound B-1

(1) Synthesis of XX-6: In a 100-mL reaction container, 2.09 g (7.4 mmol) of 1-bromo-3-iodobenzene and 1.01 g (4.9 mmol) of 4-pyridylboronic acid pinacol ester were mixed in a solvent mixture of toluene (6 mL), ethanol (3 mL), and distilled water (6 mL), and dissolved oxygen was removed by nitrogen. Subsequently, 185 mg (0.16 mmol) of Pd(PPh$_3$)$_4$ and 6 mL of an aqueous solution of 1 M sodium carbonate were added to the mixture under a nitrogen atmosphere, followed by heating at 80° C. for 6 hours for reaction.

The reaction solution was cooled to room temperature, concentrated under reduced pressure, and subjected to silica gel chromatography (mobile phase: ethyl acetate) for isolation and purification to obtain XX-6 (1.13 g).

(2) Synthesis of B-1: In a 50-mL reaction container, 113 mg (0.48 mmol) of XX-6 prepared in (1) and 80 mg (0.22 mmol) of XX-7 were mixed in a solvent mixture of toluene (6 mL) and ethanol (3 mL), wherein XX-7 is a compound synthesized using 3,4-dimethylthiophene as a starting material in accordance with the synthetic method described in Mei, Jianguo; Heston, Natha C.; Vasilyeva, Svetlana V., et al. Macromolecules, vol. 42, No. 5, pp. 1482-1487, and dissolved oxygen was removed by nitrogen. Subsequently, 24 mg (0.02 mmol) of Pd(PPh$_3$)$_4$ and 6 mL of an aqueous solution of 1 M sodium carbonate were added to the mixture under a nitrogen atmosphere, followed by heating at 100° C. for 6.5 hours for reaction.

The reaction solution was cooled to room temperature, concentrated under reduced pressure, and subjected to silica gel chromatography (mobile phase: ethyl acetate/ethanol=5/1) for isolation and purification to obtain XX-8 (51 mg).

Subsequently, 51 mg (0.12 mmol) of the resulting XX-8 and 364 mg (0.17 mmol) of benzyl bromide were dissolved in toluene (10 mL), followed by reaction at 100° C. for 6 hours.

The reaction solution was cooled to room temperature, and the resulting light yellow precipitate was collected by filtration. Ethyl acetate (40 mL) and water (50 mL) were added to the precipitate, followed by stirring. KPF$_6$ (3 g) was added to the aqueous layer, followed by an anion exchange reaction. Ethyl acetate was further added to the aqueous layer, and the organic layer was collected and concentrated to obtain target compound B-1 (41 mg). The measurement results of the NMR spectrum are shown below:

$^1$H-NMR (THF-d$_8$) δ (ppm): 9.09 (d, 4H), 8.57 (d, 4H), 8.19 (s, 2H), 8.04 (d, 2H), 7.83 (d, 2H), 7.76 (t, 2H), 7.64 (d, 4H), 7.54-7.49 (m, 6H), 5.93 (s, 4H), 2.37 (s, 6H).

The resulting exemplified compound B-1 was dissolved in chloroform. The absorption spectrum of the solution was measured as in Example 1. The maximum absorption peak λmax was observed at 311.5 nm in the ultraviolet region. Exemplified compound B-1 does not have absorption over the entire visible light region and is therefore a transparent material.

Example 3 and Comparative Example 1

Solubility in Propylene Carbonate

The solubilities of three compounds: Compound A-1 prepared in Example 1, Compound B-1 prepared in Example 2, and pyridinium salt precursor Ref-1 of Compound A-1 as a comparative example, in propylene carbonate, a solvent for an EC element, were measured.

Compound Ref-1 as a comparative example has a structure in which the pyridinium salt moiety of Compound A-1 is replaced by a non-ionized structure, a pyridyl group. The molecular structure is shown below. The results are shown in Table 1.

Ref-1

TABLE 1

| Compound No. | Solubility |
| --- | --- |
| A-1 | 300 mM or more |
| B-1 | 75 mM or more |
| Ref-1 | 8 mM or less |

The Example Compounds A-1 and B-1 had high solubility in propylene carbonate, whereas Comparative Example Compound Ref-1 not having a pyridinium salt structure caused cloud even at a concentration of 8 mM. These results demonstrate that Compounds A-1 and B-1 according to the present invention having a pyridinium salt structure as a substituent have high solubility in propylene carbonate.

<Production of Electrochromic Element and Characteristic Evaluation>

Tetrabutylammonium perchlorate serving as an electrolyte was dissolved in propylene carbonate at a concentration of 0.1 M. Subsequently, organic compound A-1 of Example 1 was dissolved in the solution at a concentration of 40.0 mM to prepare an EC solvent.

An insulating layer ($SiO_2$) was formed in the periphery of a glass substrate (lower electrode) provided with a transparent conductive film (FTO) except for an opening defining a coloring and discoloring region. A PET film (Mellinex®S, thickness: 125 μm, manufactured by Teijin DuPont Films Japan Limited) defining the distance between substrates was disposed between the glass substrate and another glass substrate (upper electrode) provided with a transparent electrode film. The periphery of the resulting element except for an opening for injection of an EC solvent was sealed with an epoxy adhesive to produce a vacant cell provided with an opening.

The EC solvent prepared above was injected into the cell from the opening by vacuum injection. The opening was sealed with an epoxy adhesive as in the periphery to provide an EC element.

The EC element immediately after the production showed a transmittance of about 80% over the entire visible light region and had high transparency.

The element applied with a voltage of 1.6 V colored by absorption (λmax=493 nm) originated from an oxidizing species of the dithienothiophene derivative as an oxidation coloring moiety. The transmittance at this wavelength during voltage application was low, 1.5%.

Furthermore, the element discolored by application with a voltage of −0.5 V. Thus, the element showed reversible coloring and discoloring. The results demonstrate that the element including the organic compound A-1 of Example 1 shows electrochromic properties giving a large difference in optical densities between coloring and discoloring due to redox.

Separately, an element was similarly produced by dissolving Compound Ref-1 of a comparative example at a concentration of 4.0 mM, and the electrochromic properties were evaluated. As a result, the transmittance at the absorption peak wavelength (494 nm) in oxidation coloring was 65%. Thus, the variation in transmittance was low.

These results demonstrate that Compound A-1 of Example 1 can achieve a large variation in transmittance in the coloring, compared to Compound Ref-1 of a comparative example.

This is caused by that Compound A-1 shows high solubility in propylene carbonate by means of the molecular structure having a pyridinium salt structure on the phenyl group in the structure.

As described above, the present invention can provide a compound not absorbing light in the visible light region in the discoloring to show high transparency and having high solubility in an organic solvent. In addition, the invention can provide an EC element including the compound and having high durability.

The organic compound according to the present invention has high transparency in the discoloring and high solubility in an organic solvent. Since the compound has high solubility in an organic solvent, the compound used in an EC element can show low transmittance in the coloring. Accordingly, the organic compound can be used in EC elements and further in optical filters, lens units, image pick-up apparatuses, and other devices including the EC elements.

Accordingly, the present invention can provide an organic compound having high solubility in an organic solvent and showing high stability against repetition of a redox reaction, and can provide an electrochromic element showing high durability by including the compound.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2013-250401 filed Dec. 3, 2013 and No. 2014-206014 filed Oct. 6, 2014, which are hereby incorporated by reference herein in their entirety.

What is claimed is:
1. An organic compound represented by Formula [1]:

[1]

wherein, $A_1$ to $A_6$ each independently represent a substituent selected from a hydrogen atom, alkyl groups having 1 to 20 carbon atoms, alkoxy groups having 1 to 20 carbon atoms, and optionally substituted aryl groups, wherein a substituent of the optionally substituted aryl group is selected from halogen atoms, alkyl groups having 1 to 4 carbon atoms, alkoxy groups having 1 to 4 carbon atoms, aryl groups, aralkyl groups, substituted amino groups, and substituted silyl groups;
n is an integer of 1 to 4;
B's each independently represent a hydrogen atom or a substituent represented by Formula [2], provided that at least one of four B's represents a substituent represented by Formula [2]:

wherein X⁻ represents an anion, and $R_2$ represents an optionally substituted alkyl group having 1 to 20 carbon atoms or an optionally substituted aryl group;

Y represents a structure represented by any one of Formulae [3] to [6], provided that when n represents a number of 2 or more, Y's are each independently selected from Formulae [3] to [6]:

wherein $R_3$ represents an alkylene group having 1 to 20 carbon atoms, and $R_4$ to $R_9$ are each independently selected from a hydrogen atom, halogen atoms, alkyl groups having 1 to 20 carbon atoms, alkoxy groups having 1 to 20 carbon atoms, optionally substituted aryl groups, alkyl ester groups having 1 to 20 carbon atoms, optionally substituted amino groups, and a cyano group.

2. The organic compound according to claim 1, wherein X⁻ is any one of $PF_6^-$, $ClO_4^-$, $BF_4^-$, $AsF_6^-$, $SbF_6^-$, $CF_3SO_3^-$, $(CF_3SO_2)_2N^-$, $Br^-$, $Cl^-$, and $I^-$.

3. The organic compound according to claim 1, wherein X⁻ is any one of $PF_6^-$, $ClO_4^-$, $BF_4^-$, and $(CF_3SO_2)_2N^-$.

4. The organic compound according to claim 1, wherein $R_2$ is a benzyl group.

5. The organic compound according to claim 1, wherein at least one of $A_1$ to $A_4$ is any one of the alkyl groups, the alkoxy groups, and the optionally substituted aryl groups.

6. An electrochromic element comprising:
a pair of electrodes; and
an electrochromic layer disposed between the pair of electrodes, wherein
the electrochromic layer includes an electrochromic compound and an electrolyte, wherein the electrochromic compound is the organic compound according to claim 1.

7. The electrochromic element according to claim 6, wherein the electrochromic layer further includes a second electrochromic compound that is a different type than the organic compound.

8. The electrochromic element according to claim 7, wherein the second electrochromic compound has a visible light transmittance in a reduced state lower than that in an oxidized state.

9. The electrochromic element according to claim 7, wherein a difference between a maximum visible-light absorptivity in the coloring and a minimum visible-light absorptivity in the coloring is 34% or less.

10. The electrochromic element according to claim 7, wherein a difference between a maximum visible-light absorptivity in the coloring and a minimum visible-light absorptivity in the coloring is 10% or less.

11. An optical filter comprising:
the electrochromic element according to claim 6; and
an active device connected to the electrochromic element.

12. A lens unit comprising:
a plurality of lenses; and
the optical filter according to claim 11.

13. An image pick-up apparatus comprising:
the optical filter according to claim 11; and
a light receiving device receiving light passed through the optical filter.

14. A window application comprising:
a pair of transparent substrates;
the electrochromic element according to claim 6 disposed between the pair of substrates; and
an active device connected to the electrochromic element.

* * * * *